Figure 1:
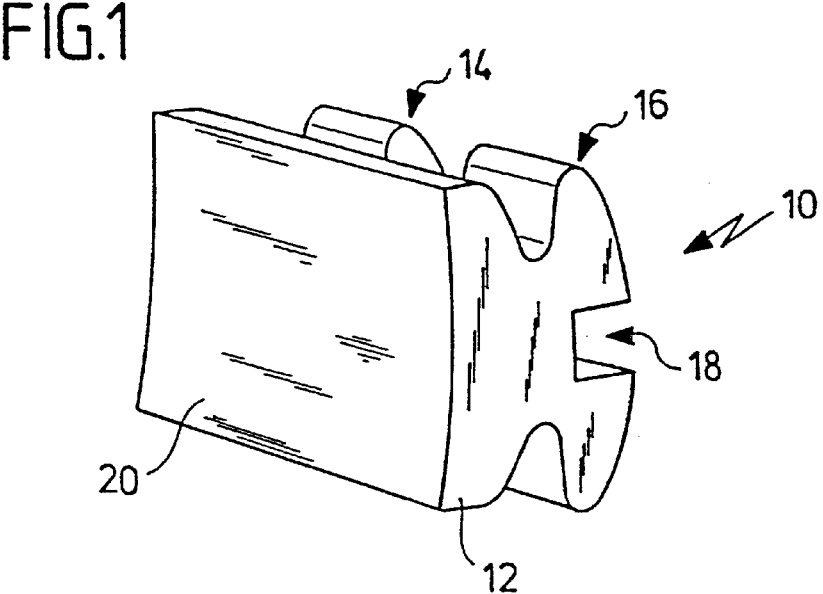

United States Patent [19]

Binder

[11] Patent Number: 5,944,517
[45] Date of Patent: Aug. 31, 1999

[54] DENTAL APPLIANCE TO BE WORN IN THE MOUTH, IN PARTICULAR IN THE FORM OF A BRACKET

[75] Inventor: Friedrich Binder, Kieselbronn, Germany

[73] Assignee: J.P. Winkelstroeter KG, Dentaurum, Ispringen, Germany

[21] Appl. No.: 09/014,205

[22] Filed: Jan. 28, 1998

Related U.S. Application Data

[63] Continuation of application No. PCT/EP95/03007, Jul. 28, 1995.

[51] Int. Cl.$^6$ .................................................. A61C 3/00
[52] U.S. Cl. .................................................. 433/9; 433/23
[58] Field of Search ........................... 433/8, 9, 23, 218

[56] References Cited

U.S. PATENT DOCUMENTS

| | | | |
|---|---|---|---|
| 4,100,678 | 7/1978 | Kenichi . | |
| 4,661,059 | 4/1987 | Kanno | 433/9 |
| 4,842,513 | 6/1989 | Bodo . | |
| 5,267,854 | 12/1993 | Schmitt | 433/9 |
| 5,267,855 | 12/1993 | Tuneberg | 433/9 |
| 5,522,725 | 6/1996 | Jordan et al. | 433/9 |
| 5,622,494 | 4/1997 | Andreiko et al. | 433/9 |

*Primary Examiner*—Todd E. Manahan
*Attorney, Agent, or Firm*—Leydig, Voit & Mayer,Ltd.

[57] ABSTRACT

Dental appliance to be worn in the mouth consisting of a meltable material, this appliance having a bonding surface to be bonded to a tooth region in a form-locking and substance-bonding manner, this surface possessing at least retention areas with recesses produced by melting the material by means of a laser beam, at least some of these recesses forming undercuts, wherein for achieving a high bonding strength the retention areas have next to the recesses a plurality of irregular elevations which are formed by the material melted during the formation of the recesses and of which at least some likewise form undercuts, wherein at least some of these elevations each have a volume equal to a fraction of the volume of the largest of these recesses. A dental appliance with a bonding surface designed in this way may be produced particularly simply when a laser beam is guided over the bonding surface in such a manner that material of the dental appliance is melted and/or vaporized at those points of the bonding surface, at which recesses are formed, is thereby ejected from the resulting recesses and forms elevations in the vicinity of the recesses.

29 Claims, 8 Drawing Sheets

DENTAL APPLIANCE TO BE WORN IN THE MOUTH, IN PARTICULAR IN THE FORM OF A BRACKET

The present application is a continuation of International Patent Application No. PCT/EP95/03007, filed Jul. 28, 1995, designating the United States, the entire specification of which is incorporated herein by reference.

So-called orthodontic accessories, such as brackets, buccal tubes and bands, serve to transfer forces to teeth and for this purpose must be secured to the teeth. This is brought about by means of an adhesive but the commercial adhesives available for this are not able to provide, without any problem, a sufficiently strong bond between the base surface of, for example, a bracket consisting of metal or ceramic material which faces the tooth, on the one hand, and adhesive, on the other hand, or between this and the tooth surface in order to transfer the desired, relatively high forces from the orthodontic accessory to the tooth. It is, therefore, necessary to provide, in addition to the chemical (substance-bonding) bond generated by the adhesive, a mechanical (form-locking) bond which is based on the principle of undercuts (so-called retentions) which are produced in the areas of orthodontic accessory and tooth to be adhered to one another and which also result in an increase in the size of the surfaces of the areas to be adhered to one another. In order to produce the smallest retentions, so-called microretentions, in that area of the tooth surface, to which the orthodontic accessory is intended to be adhered, it is customary to begin to etch the dental enamel in this area with phosphoric acid.

Retentions are most often created on the base surface of the orthodontic accessory, i.e. on the surface of, for example, a bracket body facing the tooth, as a result of the fact that a wire netting secured to a metal film or a sheet of metal is bonded to this base surface, e.g. by welding or soldering. The adhesive then penetrates into the wire netting and thereby anchors the orthodontic accessory in the hardened adhesive (cf., e.g., U.S. Pat. No. 5,295,823).

It is also already known from U.S. Pat. No. 5,295,823 to reinforce the anchoring of the orthodontic accessory provided with such a wire netting in the adhesive to an even greater degree by scarring, in addition, the surface areas of the wire netting to be wetted with the adhesive and the areas of the base surface of the orthodontic accessory not covered by this netting, either by etching, sand-blasting or shot peening or by depositing the smallest particles on these surface areas, for which purpose the most varied of methods are known from the state of the art.

All these known processes as described above for achieving the required bonding strength do, however, have, on the one hand, the disadvantage that they lead to relatively high production costs and, on the other hand, as a result of them different materials come into direct contact with one another—material of the actual orthodontic accessory, material of the wire netting, material of the particles applied to the surfaces for the purpose of increasing surface size or scarring them and, where applicable, the solder, with the aid of which the wire netting is bonded to the actual orthodontic accessory. In the mouth with the saliva as electrolyte, different metals do, however, lead to the formation of a galvanic element and thus to the corrosion of the basest of the respective metals.

In the case of metallic brackets, it is already known (DE-A-35 41 506 or EP-B-0 227 944 corresponding to this and U.S. Pat. No. 4,842,513) to cut out the so-called lobes, which include a slot between them and are arranged on a base plate, from a blank individually by means of a laser cutting device, to weld them to the base plate and to form the underside of the latter directly as a bonding surface to be adhered to the tooth, wherein the retentions required for this purpose in the bonding surface are produced by bores being worked into this bonding surface by means of a laser beam, these bores each having the shape of a circular cone with an axis inclined in relation to the bonding surface and consequently forming undercuts, behind which the adhesive can penetrate. On the one hand, it does, however, appear to be impossible on the basis of the current state of the art to produce blind bores in the shape of a circular cone by means of a laser beam, on the other hand, the bonding strengths which result when using a wire netting as adhesive base would not seem to be achievable on a bonding surface with retentions of this kind—in the last case, the bonding strength is typically between 15 and 30 $N/mm^2$ when using commercial adhesives.

Bonding problems similar to the problems described in the above for orthodontic accessories also result, however, in the case of dentures between the so-called burn-on ceramics layer and the denture portion bearing this.

The object underlying the invention was to create in a simple and inexpensive manner on a dental appliance to be worn in the mouth (intraoral) a bonding surface provided with retentions which results in the desired bonding strength without it being necessary to apply a part or parts, in particular consisting of a different material, to that part, on which the bonding surface is intended to be formed.

Proceeding on the basis of a dental appliance to be worn in the mouth which consists of a meltable material, such as that disclosed, for example, by DE-A-35 41 506, which therefore has a bonding surface to be bonded to a tooth area in a form-locking and substance-bonding manner, this bonding surface possessing at least retention areas with recesses produced by melting the material by means of a laser beam, at least some of these recesses forming undercuts, this object may be accomplished in accordance with the invention in that the retention areas have next to the recesses a plurality of irregular elevations which are formed by the material melted during the formation of the recesses and of which at least some likewise form undercuts, wherein at least some of these elevations each have a volume which is equal to a fraction of the volume of the largest of these recesses.

The invention makes use of the knowledge that when utilizing a corresponding laser and guiding the laser beam accordingly over the bonding surface the material forming the latter can be melted and/or vaporized during the production of the recesses such that it is ejected from the recesses being formed by the beam pressure and/or its own vapor pressure at that location, at which the laser beam strikes the bonding surface and is deposited again next to the recesses being formed, where applicable, however, also on the walls of the recesses being formed, and namely in the form of irregular or irregularly arranged elevations which, for their part, again form undercuts, at least in part. In this way, not only does a plurality of smaller and greater retentions result but also a considerable increase in size of the surface of the dental appliance to be wetted later with the adhesive, and tests on inventive dental appliances have shown that in this way bonding strength values of up to 60 $N/mm^2$ can be achieved without any problem, and irrespective of the material of the dental appliance whether it be a metal, a plastic or a ceramic material. It is easily apparent from the foregoing that the production of inventive retentions is much easier than in the case of the known dental appliances—in contrast to the production of the blind holes of the bracket in the shape of circular cones in accordance with DE-A-35 41 506 it is, for example, unnecessary to position and align the laser beam precisely each time in relation to the base surface of the bracket since it is important for the production of inventive retentions only that during the formation of recesses the material is ejected from the recesses just being made and is deposited again on the dental appliance in the region of the bonding surface.

Numerous advantageous developments of the invention may be attained by a corresponding choice of the laser parameters, as defined in the attached claims 2 to 20.

The use of the invention on orthodontic accessories which consist of titanium or a titanium-based alloy has proven to be particularly advantageous, especially when the orthodontic accessory has a skin consisting of a titanium compound, such as titanium oxide or titanium nitride. Advantages do, however, also result from the invention with respect to the anchoring of a ceramic layer to be burnt onto a crown or bridge framework or a plastic facing layer to be applied to this framework or with respect to the adhesion of parts of a multipart intraoral appliance which are to be secured to one another (e.g. securing the lobes of a bracket to the bracket base plate).

The invention relates, in addition, to a process for the production of an inventive dental appliance which is characterized by the fact that a laser beam is guided over the bonding surface in such a manner that the appliance material is melted and/or vaporized at those points of the bonding surface, at which recesses are formed, is thereby ejected from the resulting recesses and forms elevations in the vicinity of the recesses.

A so-called Q-switched continuous wave laser or a pulsed laser, i.e. the use of a pulsating laser beam, is particularly suitable for carrying out the inventive process; instead of this or in addition it may also be recommendable to guide the laser beam in steps over the bonding surface.

Neodymium YAG lasers or excimer lasers have proven to be particularly expedient.

It may be recommendable, in certain circumstances, to carry out the treatment with the laser beam in a protective gas atmosphere, i.e. using a gas, with which the material of the dental appliance does not react during the treatment. In the case of specific materials, such as, for example, oxide ceramics, a treatment using a reactive gas, such as, for example, oxygen, may, however, also be advantageous.

If the bonding surface treated in accordance with the invention is etched with a chemical etching agent following the laser beam treatment, the elevations previously produced are removed to a greater or lesser extent but, instead, scale-like recesses or micropores forming undercuts result in the walls of the recesses produced with the laser beam and so the bonding strength can be determined in a reproducible manner not only as a result of the choice of the laser parameters but also as a result of the choice of the type of etching agent and/or the time it acts.

With respect to the state of the art, reference is made for the sake of completeness to the following publications: DE-A-39 19 158, brochure "Concise" of the US company Dental Products/3M, article "Untersuchungen zur Verbundfestigkeit Metallplasmabeschichteter Bracketbasen" of Droese and Diedrich, journal Fortschr. Kieferorthop. 53 (1992), pages 142 to 152, published by Urban & Vogel, and article "Mechanische Mikrostrukturierung metallischer Oberflächen" of Schaller et al., journal F & M 102 (1994), pages 274 to 278, published by Carl Hanser Verlag, Munich.

Figure 2:
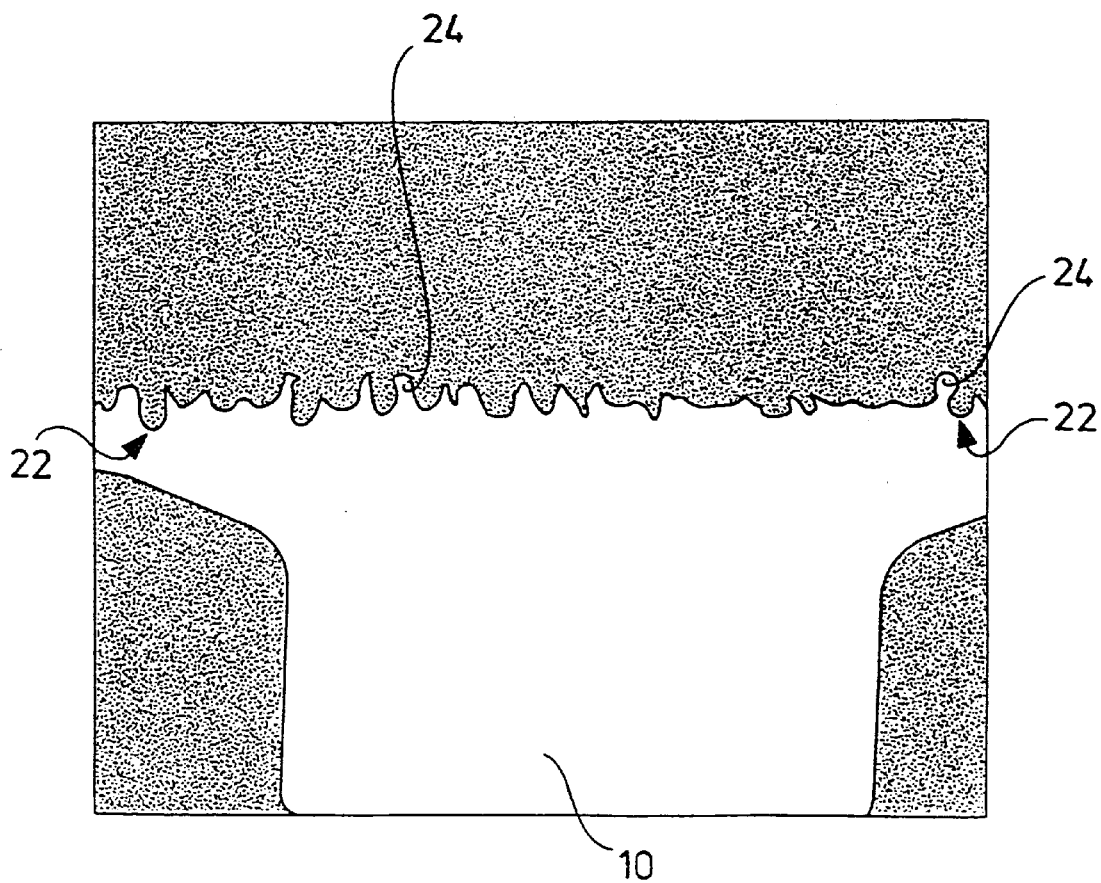
Figure 3A:
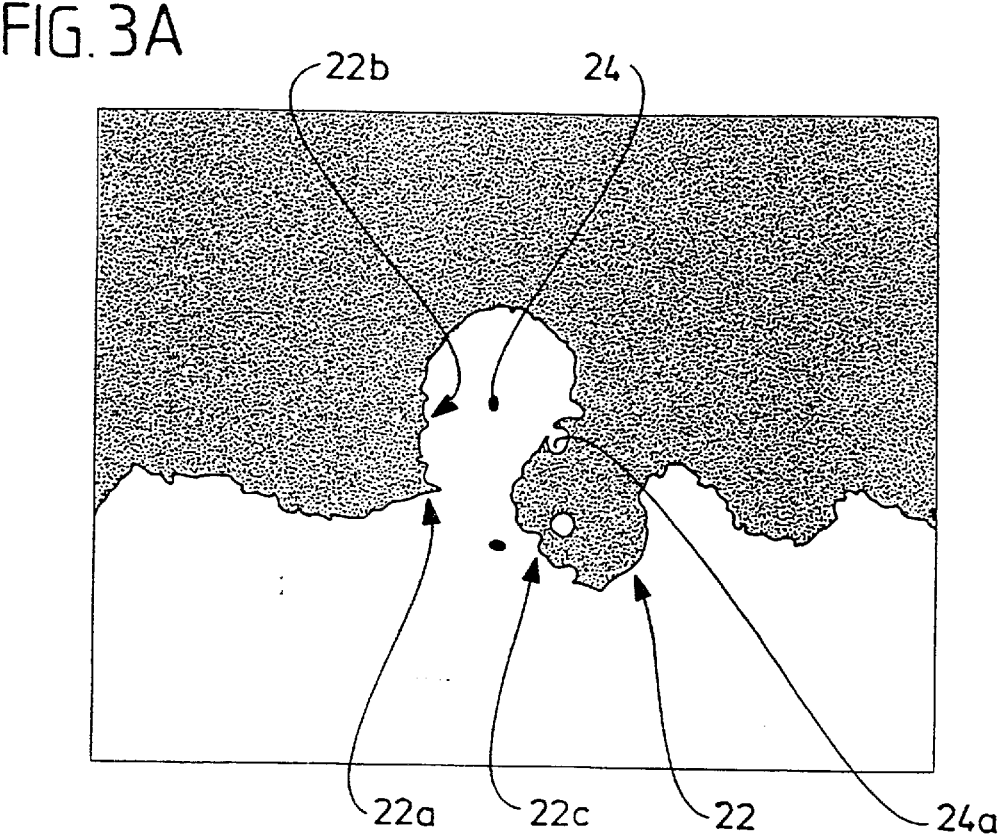
Figure 3B:
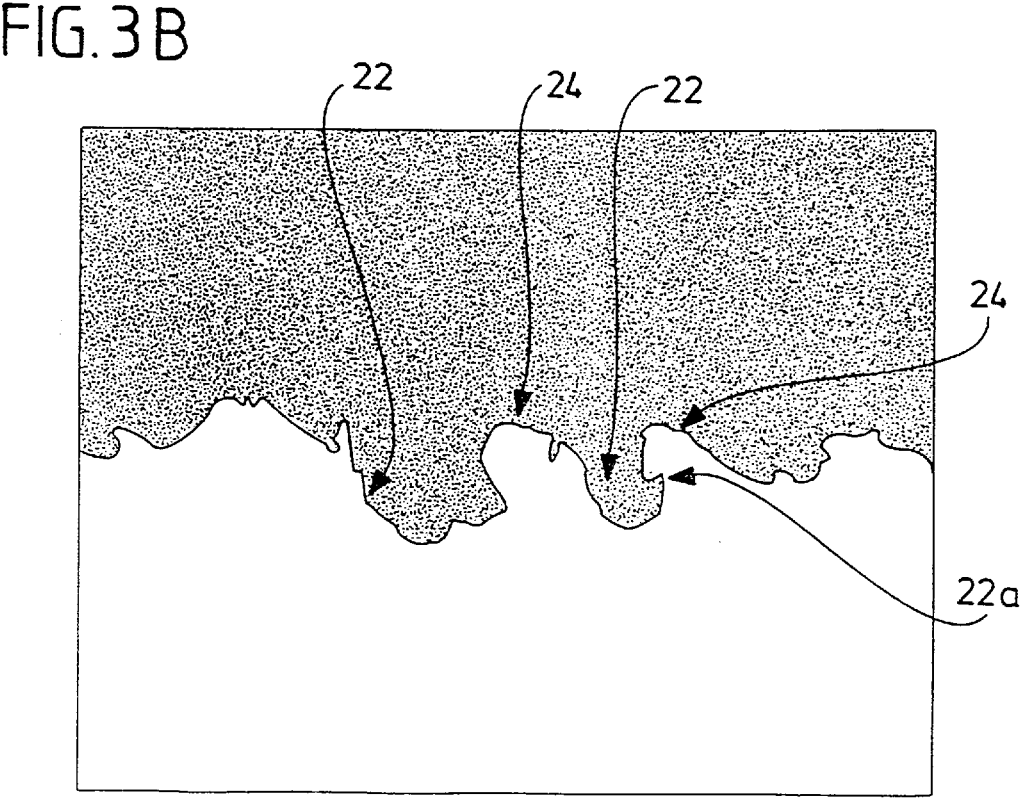
Figure 3C:
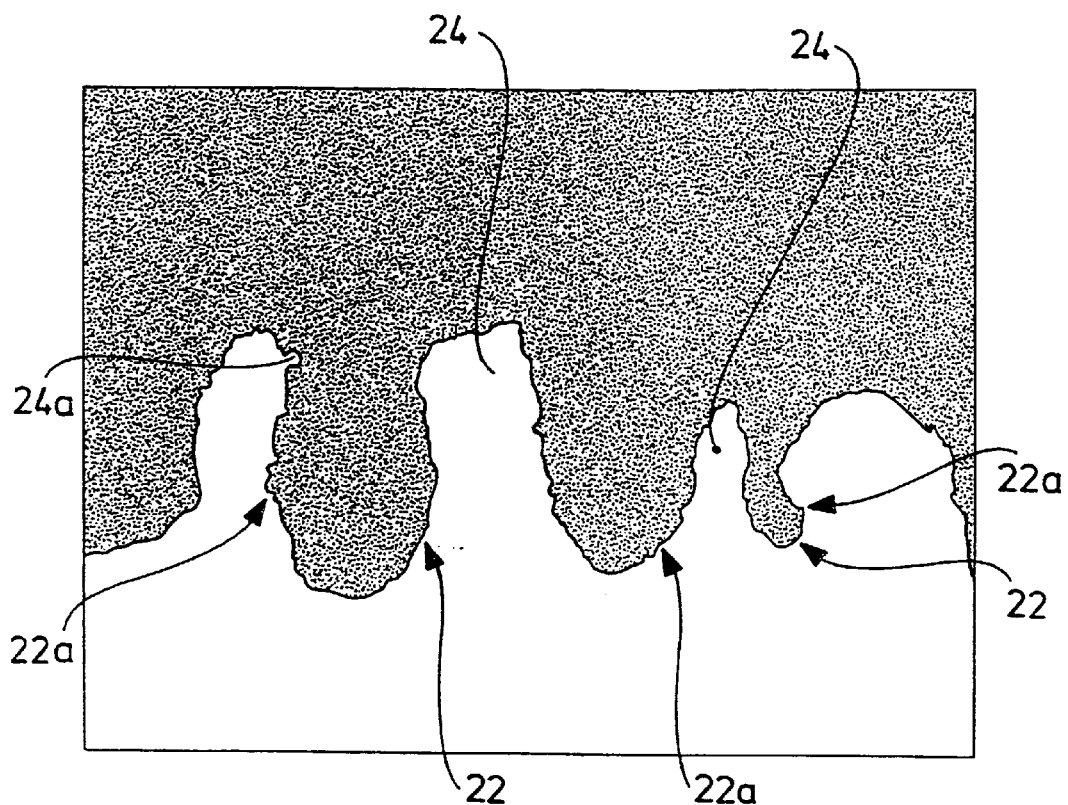

In the following, the invention will be explained in greater detail on the basis of the inventive design of the base surface of a titanium bracket serving as a direct adhesion base or rather bonding surface which is illustrated in the attached drawings and photographs; these show:

FIG. 1: a perspective illustration of the bracket, seen at an angle onto its base surface;

FIG. 2: a section through this base surface and part of the bracket, namely a section extending transversely to this base surface magnified 40 times (V=40);

FIGS. 3A, 3B and 3C: various details from FIG. 2 in the region of the base surface at V=250;

FIGS. 4 to 6C: electron microscopic photographs, namely

Figure 4:
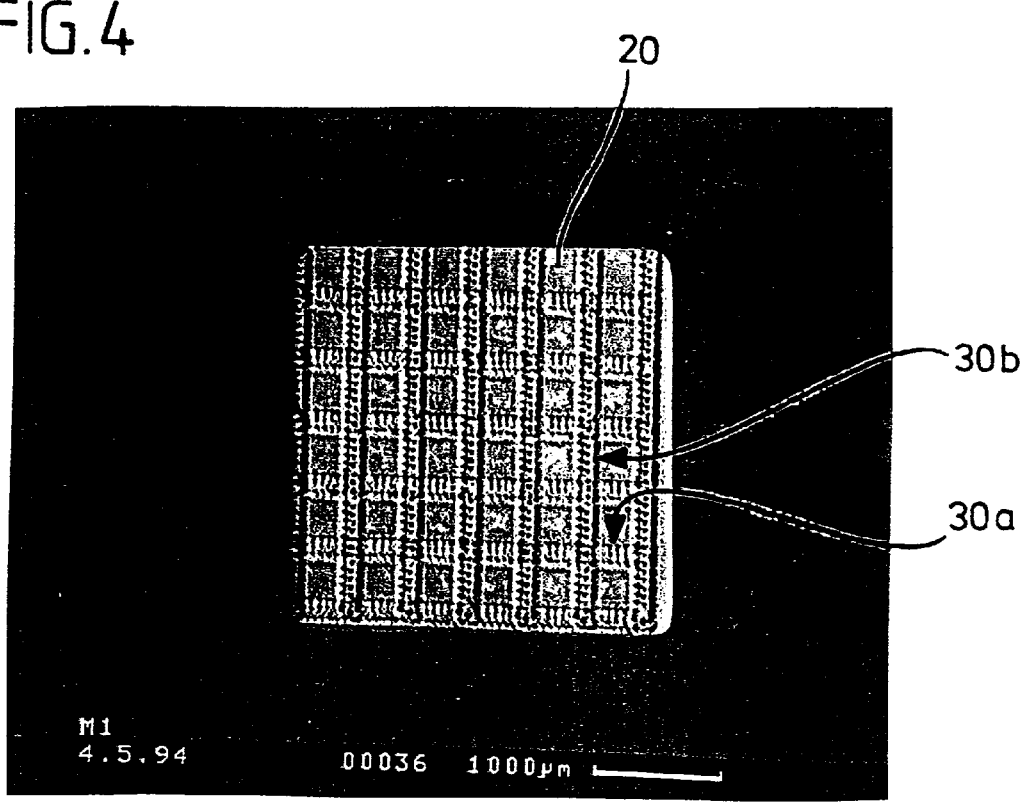
Figure 5A:
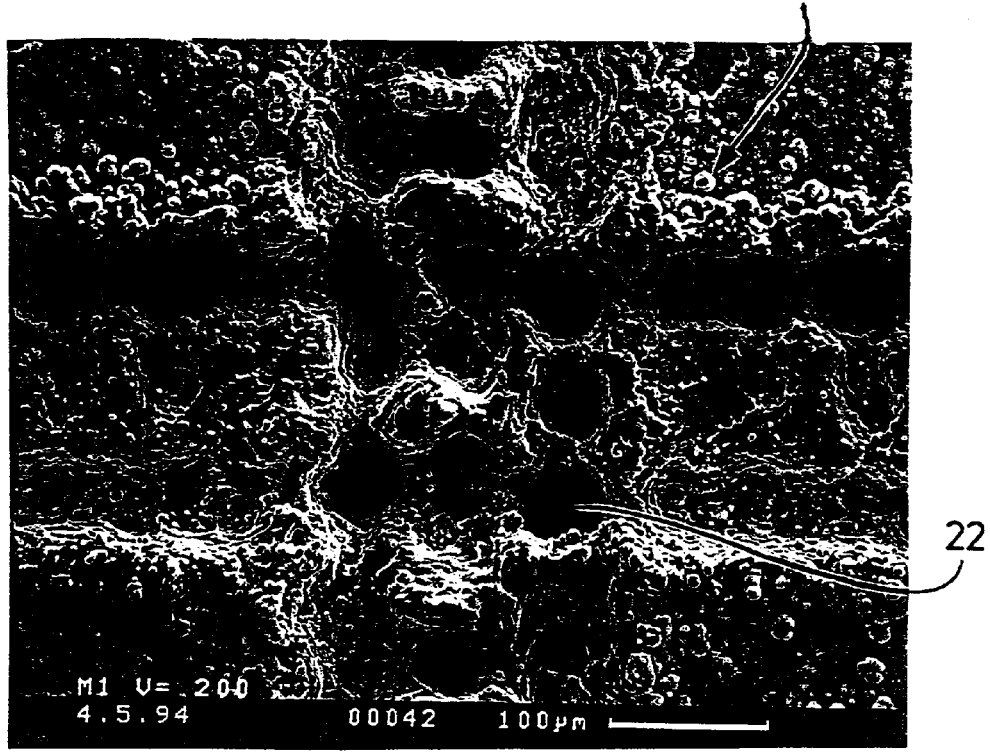
Figure 5B:
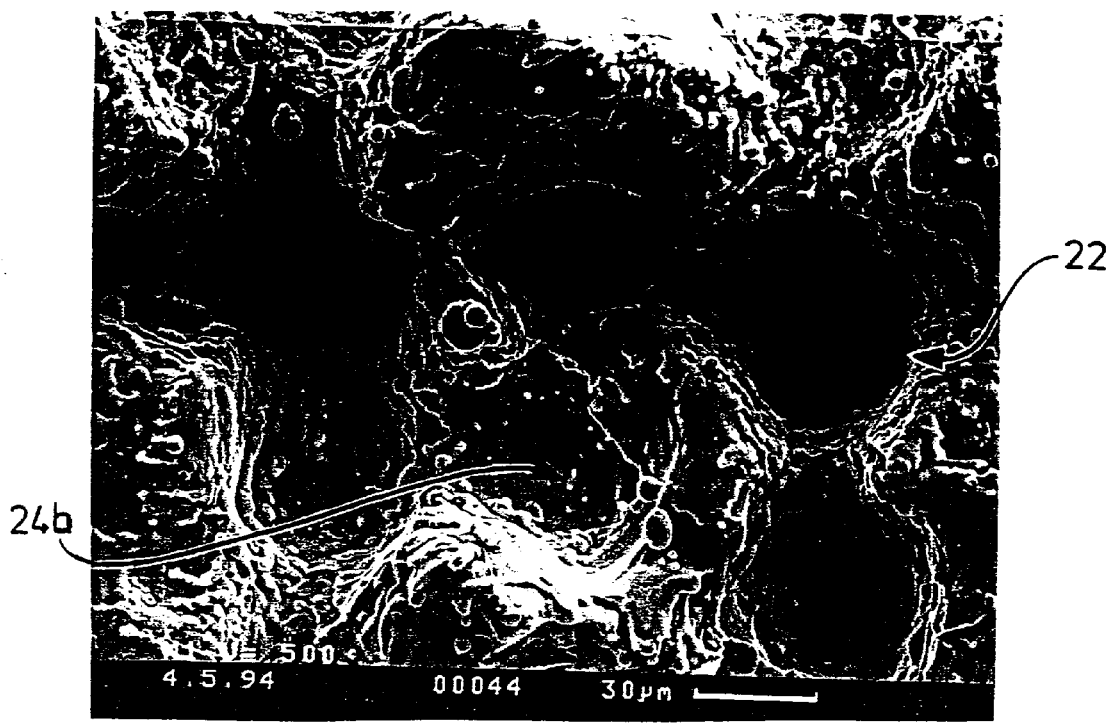
Figure 5C:
Figure 5D:
Figure 5E:
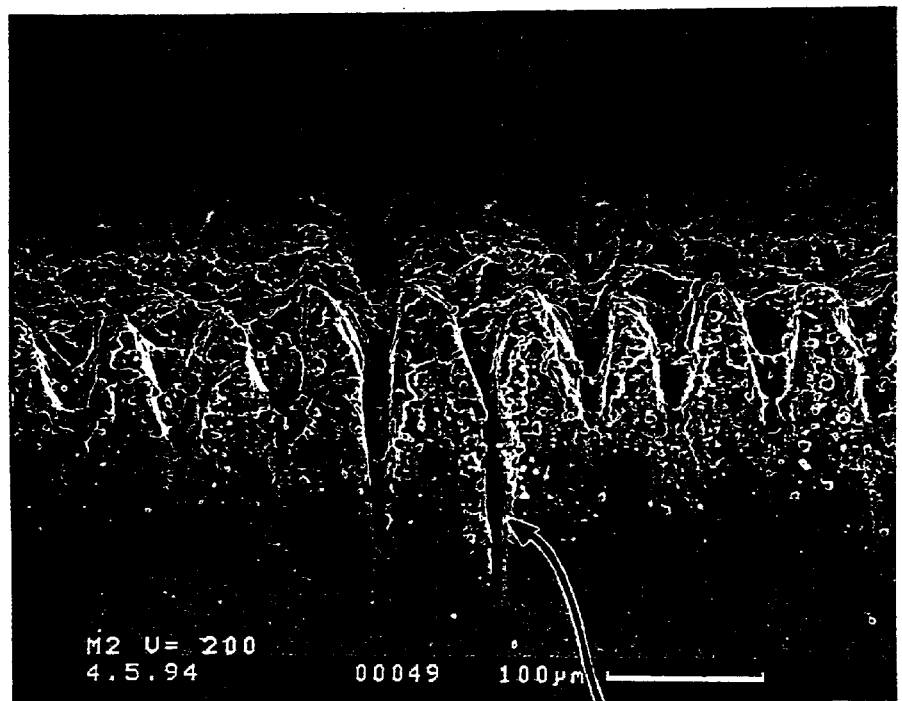
Figure 5F:
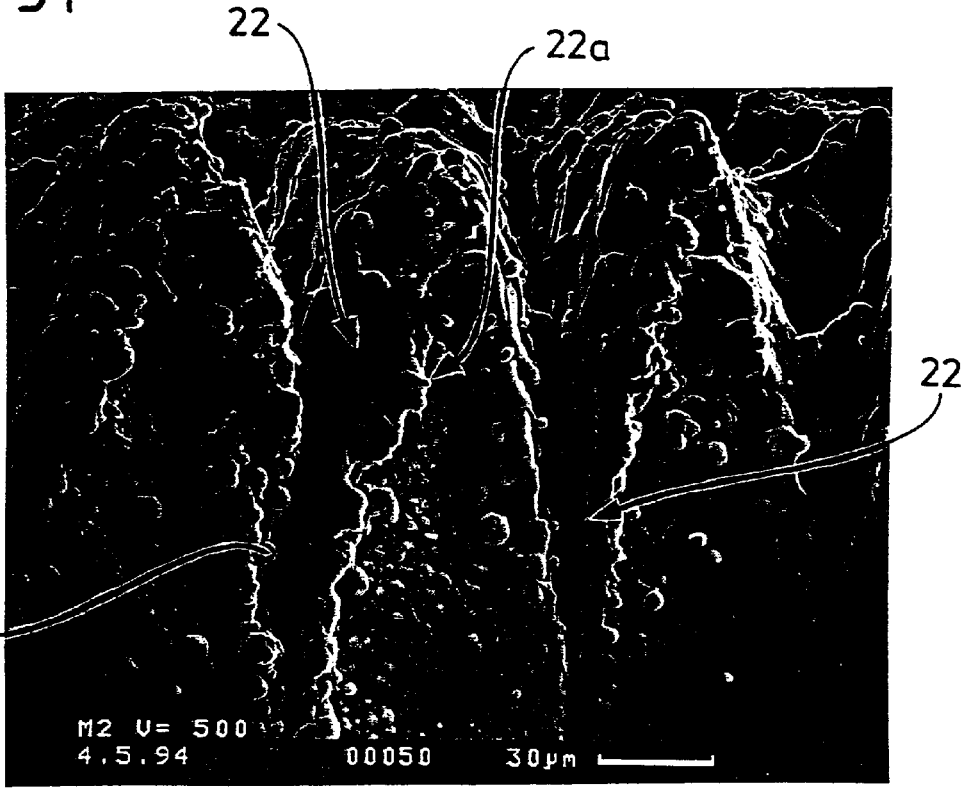
Figure 6A:
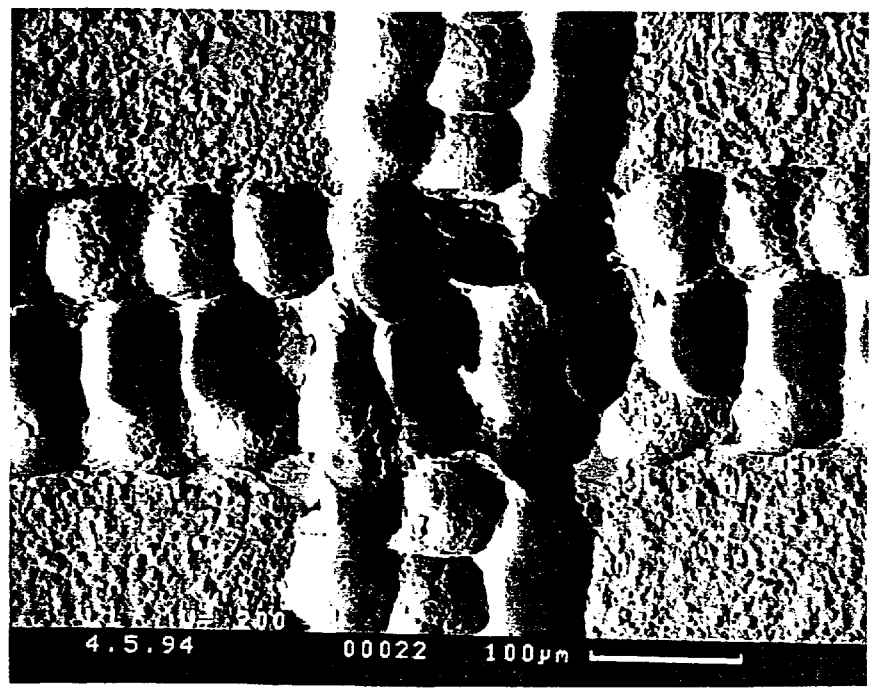
Figure 6B:
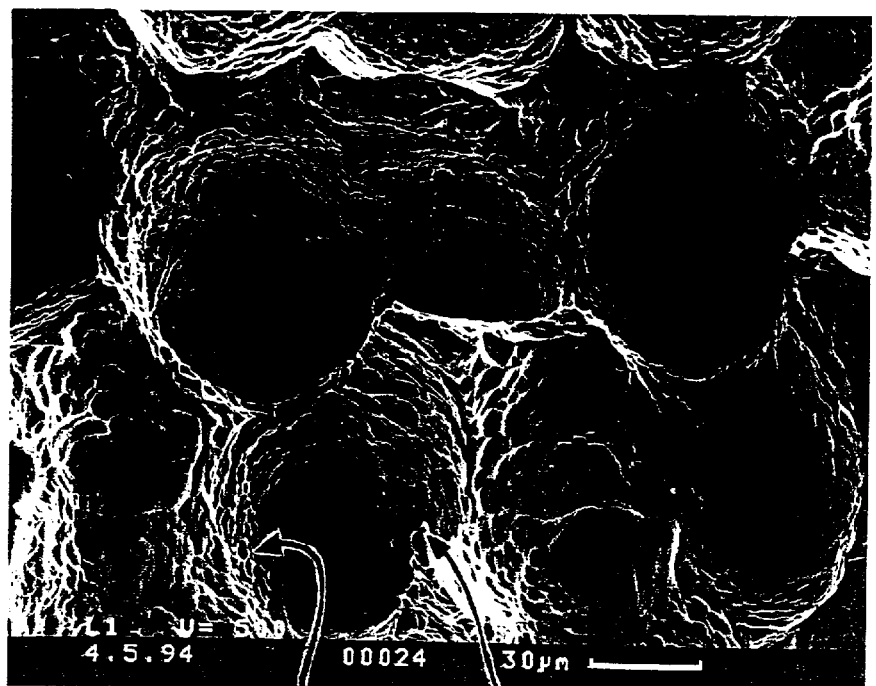
Figure 6C:
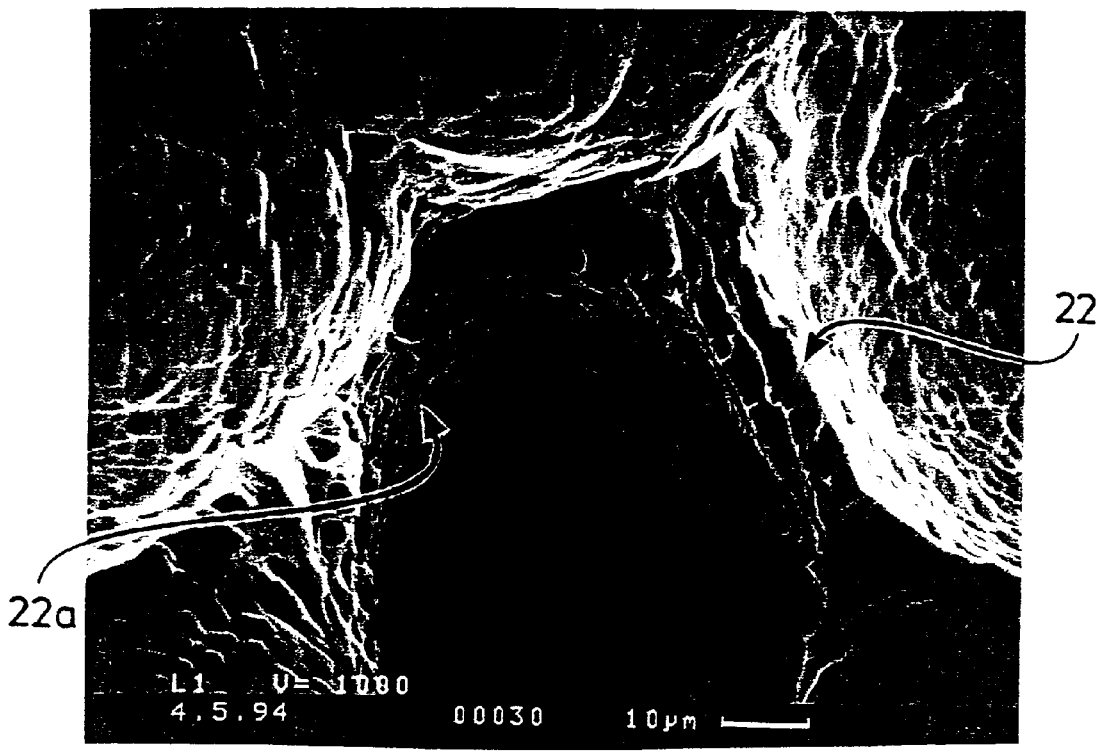

FIG. 4: a plan view of the base surface of the bracket with the retention areas forming a net-like pattern magnified 16 times (V=16);

FIG. 5A: a detail from FIG. 4, namely in an intersection area of the net-like pattern formed by the retention areas at V=200;

FIG. 5B: a detail from FIG. 5A, namely from the intersection area shown in this Figure at V=500;

FIG. 5C: a detail from FIG. 5B at V=1000;

FIG. 5D: a detail from FIG. 5A in the boundary area between a retention area and an area of the base surface adjoining this at V=500;

FIG. 5E: a side view of a retention area at V=200:

FIG. 5F: a detail from FIG. 5E at V=500;

FIG. 6A: an illustration corresponding to FIG. 5A of an intersection area at V=200, but after etching of the base surface treated by laser beam, and FIGS. 6B and 6C: a detail from FIG. 6A at V=500 and V=1000, respectively, but in a slightly angled view (inclined through 20° in relation to the vertical onto the base surface).

FIG. 1 shows a conventional bracket designated as a whole as 10 and consisting of titanium or a titanium-based alloy which has on a base plate 12 two lobes 14 and 16 which form a slot 18 for the insertion of a wire. The underside of the bracket 10 or the base plate 12 later facing the tooth represents the base surface 20 of the bracket which is intended, in the case of an inventive bracket, to represent at the same time its bonding surface to be bonded directly to a tooth by means of an adhesive.

In the detail illustrated in FIG. 2 from a section through the bracket 10 now treated in accordance with the invention at right angles to the bonding surface 20, the latter has been turned upwards, and FIG. 2 already shows a plurality of inventively configured retentions. In the following, the comparatively large recesses in the form of blind holes as well as the comparatively large elevations in the form of molten pearls or the like are designated as macroretentions insofar as these recesses and elevations form undercuts and thus can develop a retentive effect for the anchoring of the bracket in the adhesive layer. Structures which likewise form undercuts but are relatively small are designated as microretentions, these structures having, in particular, the shape of small recesses in the walls of the coarse recesses produced by means of the laser beam, but also in the surfaces of the elevations present in accordance with the invention.

FIG. 2 shows macroretentions in the form of recesses 22 and elevations 24.

FIG. 3A shows the two macroretentions designated in FIG. 2 to the right as 22 and 24 in the form of a recess 22 and an elevation 24 but also shows microretentions as a result of the greater magnification, namely not only in the wall of the recess 22 but also in and on the surface of the elevation 24, and some of these microretentions in the form of smallest recesses have been designated as 22a, 22b and 22c while at 24a a microretention is shown in the form of a small elevation on the surface of the macroretention 24. In FIGS. 3B and 3C, the macroretentions and microretentions have been allocated the same reference numerals 22 and 24 as well as 22a and 24a.

Whereas FIG. 1 is intended to illustrate the bonding surface 20 prior to the laser beam treatment, FIG. 4 shows the bonding surface 20 after the laser treatment. FIG. 4 thereby shows the case where the laser beam has been guided in a grid-like, i.e. net-like pattern over the bonding surface 20 and so the retention areas corresponding to the laser tracks form a net-like pattern on or in the bonding surface 20. In FIG. 4, a host of retention areas 30a extending horizontally and parallel to one another forms this net-like pattern together with a host of retention areas 30b extending vertically and parallel to one another. FIG. 5A now shows in a greater magnification than FIG. 4 that part of the bonding surface 20 located in the region of an intersection of a retention area 30a with a retention area 30b. In FIG. 5A, macroretentions in the form of recesses 22 and elevations 24 located next to these are clearly apparent, wherein these elevations are bulge-like or ball-shaped deposits, in particular molten pearls, of the bracket material.

FIGS. 5B and 5C taken at a greater magnification again show macroretentions in the form of recesses 22 but also microretentions in the form of recesses 22a and smallest elevations 24b.

FIG. 5D shows very clearly how macroretentions in the form of elevations 24 are arranged on the bonding surface 22 in a region of the bonding surface which is located to the right next to a retention area 30b with macroretentions in the form of recesses 22.

FIGS. 5E and 5F show macroretentions in the form of capillary recesses 22, in the walls of which microretentions are formed in the shape of smallest recesses 22a, on the walls of which microretentions have also been deposited in the form of smallest elevations 24a.

FIG. 6A corresponding to FIG. 5A shows that following etching of the bonding surface 20 treated with the laser beam the latter does have a considerable increase in the size of its surface in comparison to its original state but the surface structures produced by the laser beam treatment have been smoothed to a considerable degree. On the other hand, the detail from FIG. 6A shown in FIG. 6B shows that the walls of the macroretentions in the form of recesses 22 have a plurality of microretentions in the form of smallest, scale-like recesses 22a. FIG. 6C shows this surface structure at an even greater magnification.

It is apparent from this that the object of the present invention is also an intraoral appliance, in which recesses produced with a laser beam, in the walls of which microretentions resulting due to etching and in the form of smallest recesses are located, are present in a bonding surface, on which a layer consisting of adhesive or a different coating material (burn-on ceramics, plastics or the like) is to be anchored.

In accordance with the invention, the material of the bonding surface of the dental appliance which is first of all smooth is locally melted and/or vaporized by means of a laser beam, in particular in a grid-like manner; during this local melting or vaporizing material is ejected from the bonding surface during the course of formation of recesses in this surface, namely under the influence of the beam pressure or the intrinsic vapor pressure of the material at that point, at which the laser beam strikes the bonding surface. The material thereby ejected is deposited again next to the recesses and/or on their walls and forms elevations, in particular in the form of small and smallest molten pearls.

Depending on the setting of the laser parameters, a distinct scoring of the bonding surface with macroretentions and microretentions is obtained, the undercuts of which, together with the distinct increase in surface size, lead to a secure anchoring, for example, of a bracket in an adhesive layer.

It has been shown that so-called inscribing lasers are best suited for carrying out the inventive process, these being preferred to the lasers customarily used for welding. Lasers with a power of less than 20 Watts are particularly suitable.

As is apparent from the preceding description and the attached pictures, use is actually made in the present invention of the otherwise undesired faults of a laser beam treatment—material ejected from the workpiece should remain on the workpiece at least for the most part in order to form additional retentions on it, an effect which is not mentioned anywhere in the state of the art even by way of allusion.

I claim:

1. A dental appliance to be worn in the mouth comprising a meltable material having a bonding surface to be bonded to a tooth region in a form-locking and substance-bonding manner, said bonding surface possessing at least retention areas with recesses produced by melting the material by means of a laser beam, at least some of said recesses forming undercuts, wherein the retention areas have next to the recesses a plurality of irregular elevations formed by the material melted during the formation of the recesses, at least some of the elevations likewise forming undercuts, wherein at least some of these elevations each have a volume equal to a fraction of the volume of the largest of these recesses.

2. The appliance of claim 1, wherein the plurality of the elevations each has a volume equal to a fraction of the volume of the largest recess.

3. The appliance of claim 1, wherein the recesses are of different shapes.

4. The appliance of claim 1, wherein the elevations are of different shapes.

5. The appliance of claim 1, wherein the recesses are arranged irregularly within a retention area.

6. The appliance of claim 1, wherein the elevations are arranged irregularly within a retention area.

7. The appliance of claim 1, wherein some of the recesses each have a volume equal to a fraction of the volume of the largest recess.

8. The appliance of claim 1, wherein some of the elevations each have a volume equal to a fraction of the volume of the largest elevation.

9. The appliance of claim 1, wherein in the case of at least some of the recesses the wall of the recess has an irregular shape.

10. The appliance of claim 1, wherein in the case of at least some of the elevations their surface has an irregular shape.

11. The appliance of claim 1, wherein in the case of at least some of the recesses microrecesses are located in the recess wall.

12. The appliance of claim 1, wherein in the case of at least some of the recesses microelevations are located on the recess wall.

13. The appliance of claim 1, wherein in the case of at least some of the elevations microrecesses are located in their surface.

14. The appliance of claim 1, wherein in the case of at least some of the elevations microelevations are located on their surface.

15. The appliance of claim 1, wherein the retention areas form a striped pattern on the bonding surface.

16. The appliance of claim 15, wherein the retention areas form a net-like pattern on the bonding surface.

17. The appliance of claim 16, wherein the retention areas are designed with recesses and elevations on at least one of several bonding surfaces to be adhered to one another of parts of an intraoral appliance to be secured to one another.

18. The appliance of claim 16, wherein the bonding surface is formed on a crown or bridge framework to be provided with burn-on ceramics or a plastics facing.

19. The appliance of claim 1, wherein the bonding surface is the base surface of an orthodontic accessory in the form of a bracket, a buccal tube or a band, said base surface to be bonded to a tooth by means of an adhesive.

20. The appliance of claim 19, wherein the orthodontic accessory consists of titanium or a titanium-based alloy.

21. The appliance of claim 20, wherein the orthodontic accessory has a skin consisting of a titanium compound.

22. A method for manufacturing the dental appliance of claim 1, wherein a laser beam is guided over the bonding surface in such a manner that appliance material is melted and/or vaporized at those points of the bonding surface where recesses are formed, is thereby ejected from the resulting recesses and forms elevations in the vicinity of the recesses.

23. The method of claim 22, wherein a Q-switched continuous wave laser or a pulsed laser is used.

24. The method of claim 22, wherein the laser beam is guided in steps over the bonding surface.

25. The method of claim 22, wherein a neodymium YAG laser is used.

26. The method of claim 22, wherein an excimer laser is used.

27. The method of claim 22, wherein the treatment with the laser beam is carried out in a protective gas atmosphere.

28. The method of claim 22, wherein the treatment with the laser beam is carried out using a gas reacting with the material of the bonding surface during the treatment.

29. The method of claim 22, wherein the bonding surface is etched with an etching agent following the laser beam treatment.

* * * * *